(12) United States Patent
Schader et al.

(10) Patent No.: US 12,274,868 B2
(45) Date of Patent: Apr. 15, 2025

(54) FEEDBACK MECHANISM FOR AN INJECTION DEVICE

(71) Applicant: Sanofi-Aventis Deutschland GMBH, Frankfurt am Main (DE)

(72) Inventors: Marc Schader, Frankfurt am Main (DE); Matthias Rau, Rüsselsheim (DE); Sebastian Braun, Rüsselsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/509,732

(22) Filed: Nov. 15, 2023

(65) Prior Publication Data

US 2024/0108810 A1    Apr. 4, 2024

Related U.S. Application Data

(63) Continuation of application No. 16/346,242, filed as application No. PCT/EP2017/076097 on Oct. 12, 2017, now Pat. No. 11,865,315.

(30) Foreign Application Priority Data

Nov. 1, 2016    (EP) .................................... 16196674

(51) Int. Cl.
 *A61M 5/315*    (2006.01)
 *A61M 5/145*    (2006.01)
 *A61M 5/20*    (2006.01)
(52) U.S. Cl.
 CPC ...... *A61M 5/31565* (2013.01); *A61M 5/2033* (2013.01); *A61M 5/3157* (2013.01);
 (Continued)

(58) Field of Classification Search
 CPC ............ A61M 5/31566; A61M 5/3157; A61M 5/31565; A61M 5/2033; A61M 2205/581;
 (Continued)

(56) References Cited

U.S. PATENT DOCUMENTS 5,921,962 A * 7/1999 Kriesel ............... A61M 31/002
  604/890.1
2002/0007671 A1   1/2002 Lavi et al.
  (Continued)

FOREIGN PATENT DOCUMENTS

CN        102137692        7/2011
CN        102917738        2/2013
       (Continued)

OTHER PUBLICATIONS

International Preliminary Report on Patentability in International Application No. PCT/EP2017/076097, dated May 7, 2019, 7 pages.
(Continued)

*Primary Examiner* — Michael J Tsai
*Assistant Examiner* — Neeraja Gollamudi
(74) *Attorney, Agent, or Firm* — Fish & Richardson P.C.

(57) ABSTRACT

A feedback mechanism for an injection device that is configured to deliver a medicament to a user is described. The feedback mechanism comprises an actuator and a fluid chamber having a restricted outlet. The actuator is adapted to urge fluid from the fluid chamber through the restricted outlet. The feedback mechanism also has an indicator that is adapted to provide feedback to the user after a predetermined volume of fluid has passed from the fluid chamber through the restricted outlet during use of the injection device.

20 Claims, 13 Drawing Sheets

(52) U.S. Cl.
CPC ..... *A61M 5/1452* (2013.01); *A61M 2205/581* (2013.01); *A61M 2205/583* (2013.01)

(58) Field of Classification Search
CPC .......... A61M 2205/583; A61M 5/1452; A61M 5/1684; A61M 2205/58; A61M 5/315; A61M 2005/31598
See application file for complete search history.

(56) References Cited

U.S. PATENT DOCUMENTS

| | | |
|---|---|---|
| 2012/0310169 A1 | 12/2012 | Sonderegger et al. |
| 2013/0066274 A1* | 3/2013 | O'Connor ......... A61M 5/16877 604/151 |
| 2013/0090605 A1 | 4/2013 | O'Connor et al. |
| 2013/0218093 A1 | 8/2013 | Markussen et al. |
| 2014/0094754 A1 | 4/2014 | Servansky |
| 2015/0057613 A1 | 2/2015 | Clemente et al. |
| 2015/0094674 A1* | 4/2015 | Pratt ....................... A61M 1/96 604/319 |
| 2016/0250411 A1 | 9/2016 | Nessel et al. |

FOREIGN PATENT DOCUMENTS

| | | | |
|---|---|---|---|
| CN | 105025965 | 11/2015 | |
| EP | 3067081 | 9/2016 | |
| EP | 3067081 A1 * | 9/2016 | ............. A61M 5/20 |
| JP | 2012-500695 | 1/2012 | |
| JP | 2017-500083 | 1/2017 | |
| JP | 2017-514585 | 6/2017 | |
| JP | 2017-528217 | 9/2017 | |
| WO | WO 2010/023303 | 3/2010 | |
| WO | WO 2011/123024 | 10/2011 | |
| WO | WO 2014/139916 | 9/2014 | |
| WO | WO 2015/074977 | 5/2015 | |
| WO | WO 2015/165991 | 11/2015 | |
| WO | WO 2015/166286 | 11/2015 | |
| WO | WO 2015/185311 | 12/2015 | |
| WO | WO 2016/027096 | 2/2016 | |
| WO | WO 2016/034407 | 3/2016 | |

OTHER PUBLICATIONS

International Search Report and Written Opinion in International Application No. PCT/EP2017/076097, dated Jan. 25, 2018, 11 pages.

* cited by examiner

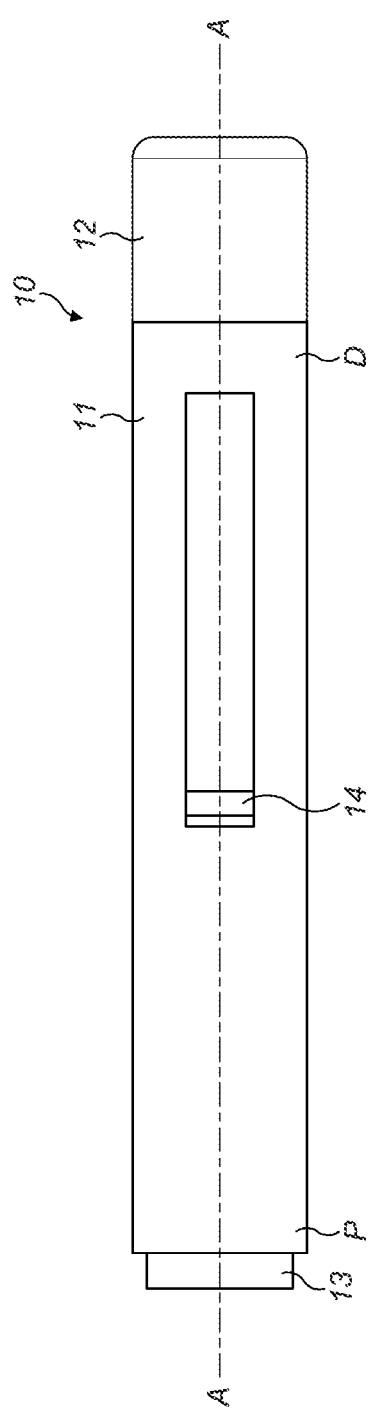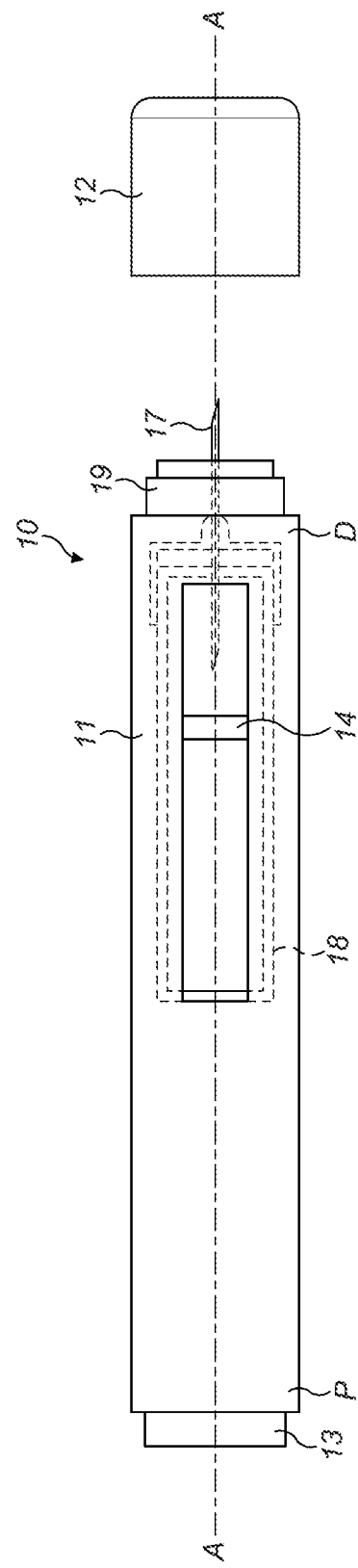

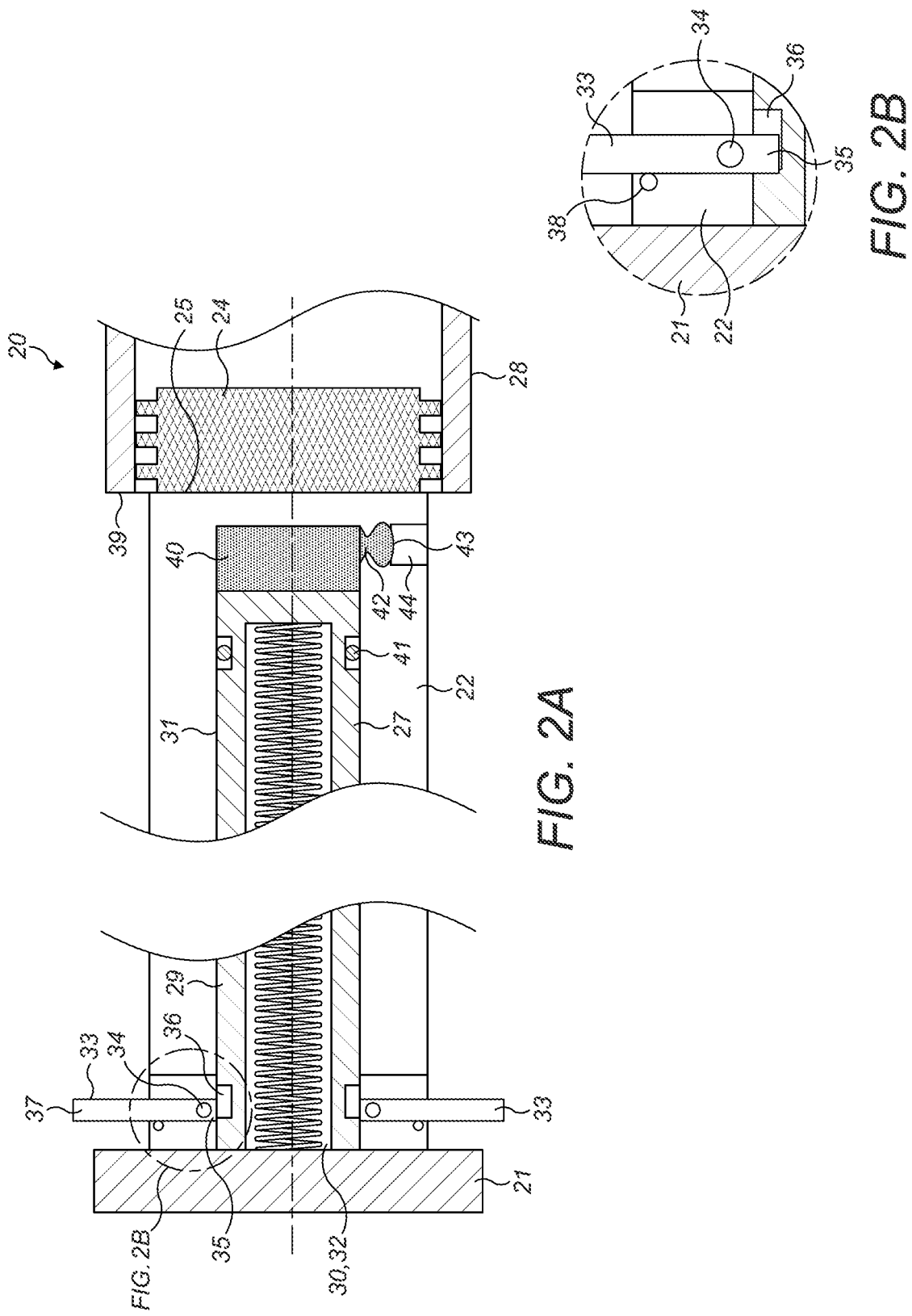

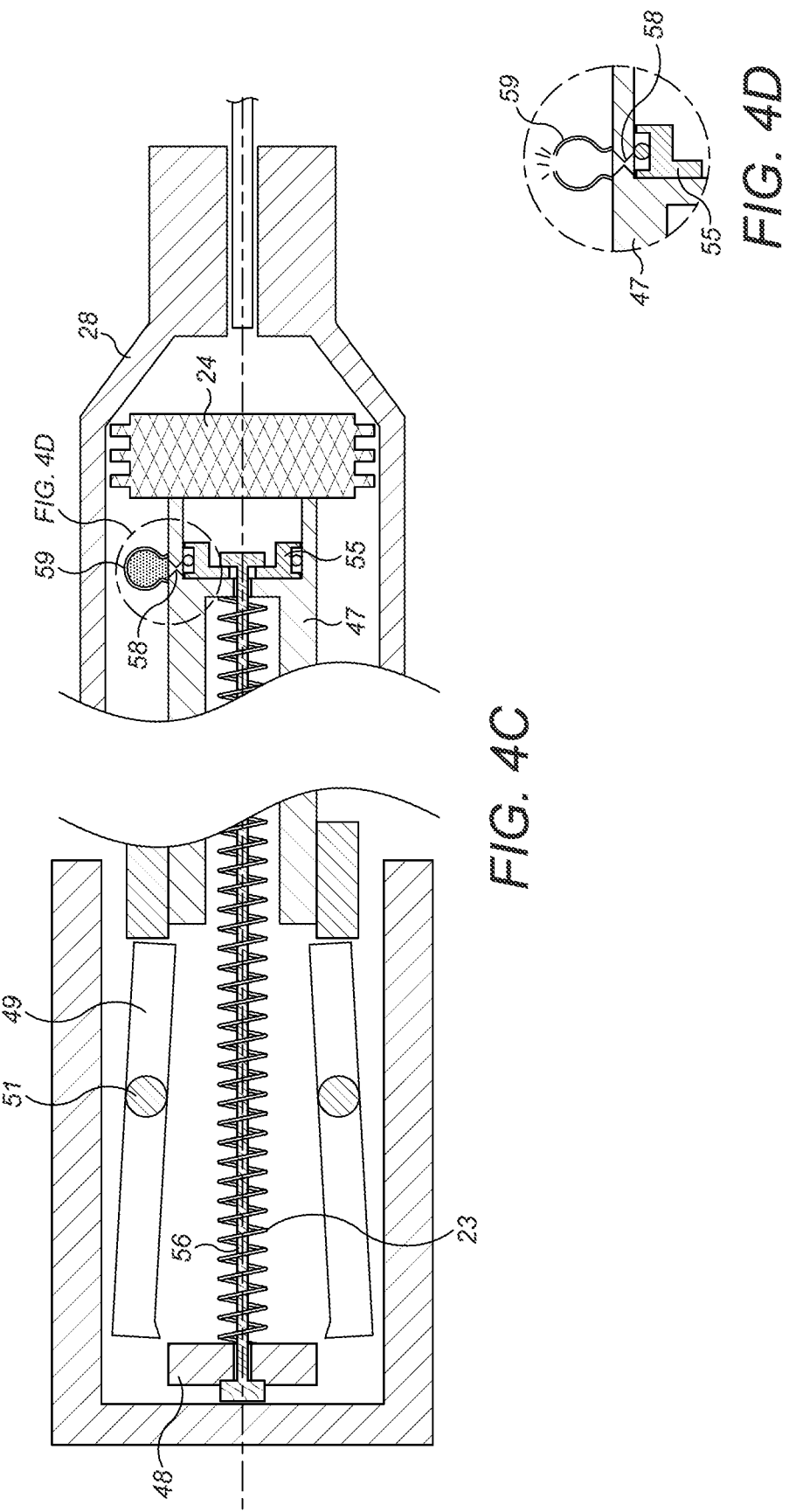

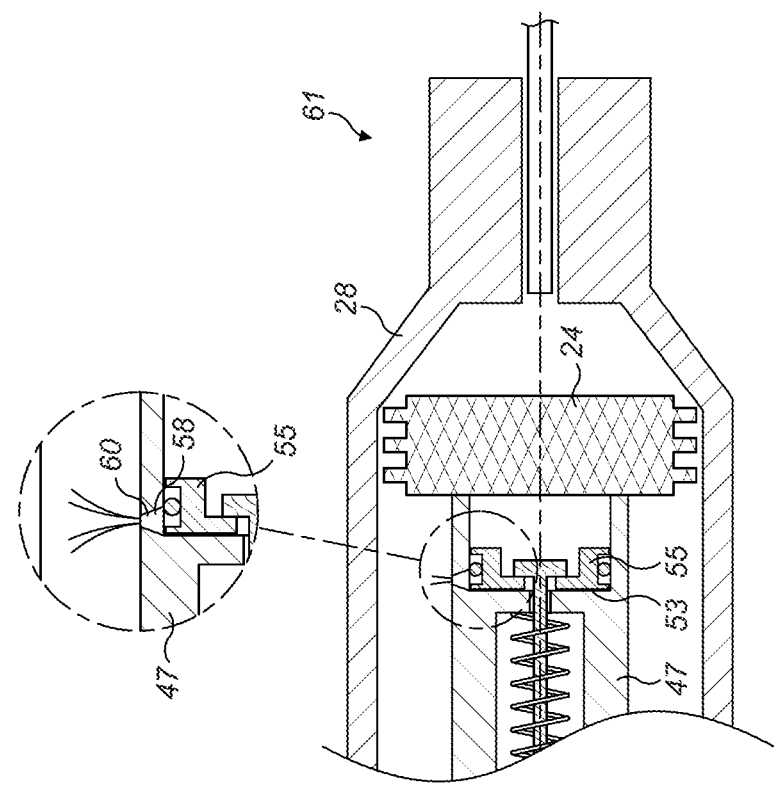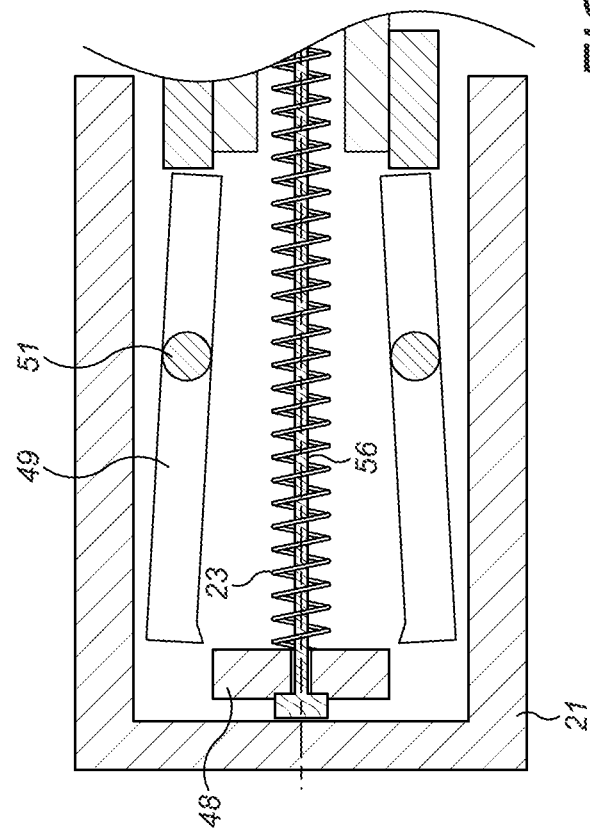
FIG. 5

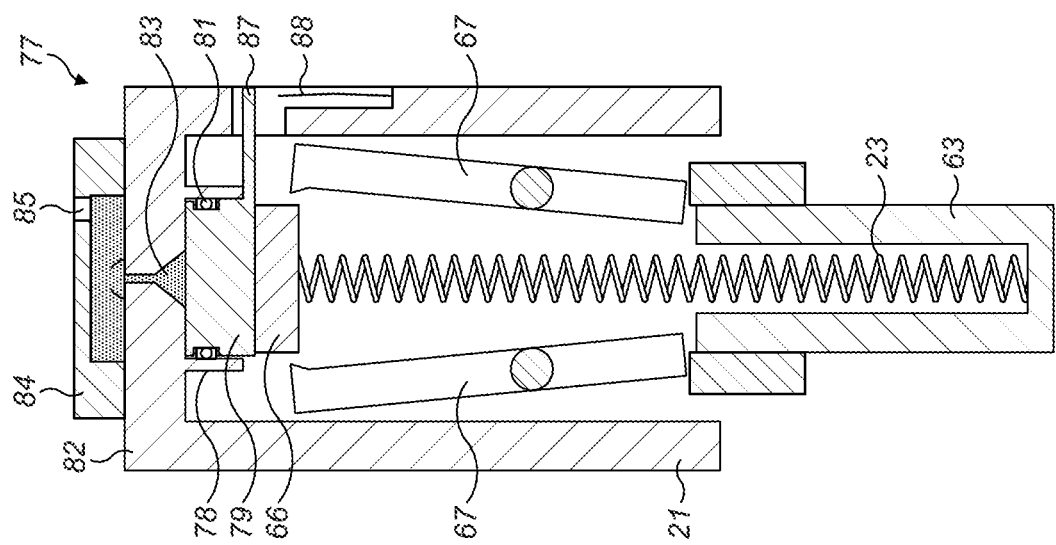
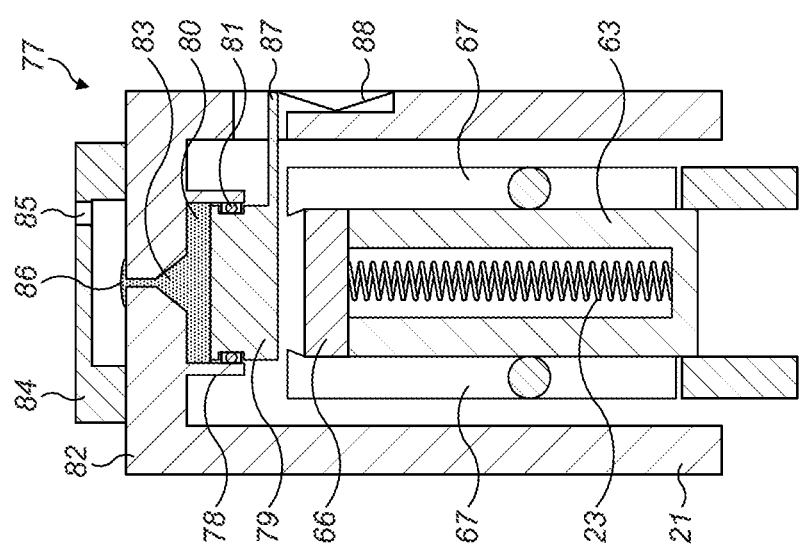

FEEDBACK MECHANISM FOR AN INJECTION DEVICE

CROSS REFERENCE TO RELATED APPLICATIONS

The present application is a continuation of U.S. patent application Ser. No. 16/346,242, filed Apr. 30, 2019, which is the national stage entry of International Patent Application No. PCT/EP2017/076097, filed on Oct. 12, 2017, and claims priority to Application No. EP 16196674.2, filed on Nov. 1, 2016, the disclosures of which are incorporated herein by reference.

TECHNICAL FIELD

The present disclosure relates to a feedback mechanism for an injection device.

BACKGROUND

Injection devices, such as auto-injectors, typically have a syringe into which a plunger is pushed to dispense medicament from the syringe into the patient via a needle. The injection process is completed when the plunger has been pushed the appropriate distance into the syringe. It is known to provide a feedback mechanism for indicating to the user when the appropriate volume of medicament has been injected.

SUMMARY

It is an object of the present disclosure to provide a feedback mechanism for an injection device that provides delayed feedback to a user, at a time after the medicament has been injected.

According to a first aspect, there is provided a feedback mechanism for an injection device, said injection device being configured to deliver a medicament to a user, the feedback mechanism comprising an actuator and a fluid chamber having a restricted outlet, wherein the actuator is adapted to urge fluid from the fluid chamber through the restricted outlet; and, an indicator adapted to provide feedback to said user after a predetermined volume of fluid has passed from the fluid chamber through the restricted outlet during use of the injection device.

In some examples, the indicator comprises a shaped passage adapted to create an audible sound as fluid passes through the shaped passage.

In other examples, the indicator comprises a membrane adapted to be inflated by fluid passing through the restricted outlet.

The membrane may be adapted to be burst by fluid passing through the restricted outlet.

The indicator may comprise a second chamber adapted to receive fluid passing through the restricted outlet.

In some examples, at least a part of the second chamber is adapted to be displaced by fluid passing into the second chamber.

In other examples, at least a part of the second chamber is transparent or translucent such that a user can see fluid passing into the second chamber.

According to another aspect, there is also provided an injection device comprising a medicament delivery mechanism comprising a reservoir and a plunger that moves to displace medicament from the reservoir for delivery to a user during use of the injection device; and, the feedback mechanism as described above.

The actuator may be adapted to move into the fluid chamber after the plunger has reached a pre-determined position. Alternatively, the actuator may be adapted to move into the fluid chamber after a pre-determined amount of medicament has been displaced from the reservoir.

The injection device may further comprise a locking mechanism having a first position in which the locking mechanism holds the actuator, and a second position in which the locking mechanism releases the actuator such that the actuator urges fluid from the fluid chamber.

The locking mechanism may comprise a locking arm that engages the actuator during delivery of said medicament, and the locking arm may be arranged to disengage the actuator after said medicament has been delivered.

The locking arm may comprise a pivot that permits the locking arm to rotate out of engagement with the actuator, and a stop arranged to prevent rotation of the locking arm until said medicament has been delivered.

The locking mechanism may be configured to release the actuator when the plunger has moved to a pre-determined position during delivery of said medicament.

The reservoir may contain a medicament.

In some examples, the indicator is adapted to provide feedback to said user at a predetermined time after medicament has been delivered to the user. For example, the feedback may be provided more than 2 seconds after the medicament has been delivered to the user, or feedback may be provided more than 5 seconds after the medicament has been delivered to the user, or feedback may be provided more than 10 seconds after the medicament has been delivered to the user.

In some examples, the injection device is an auto-injector. In other examples, the injection device is a pen-injector. In other examples, the injection device is a large-volume device.

According to a further aspect, there is also provided a method of using an injection device, the method comprising:
delivering medicament to a user;
urging fluid from a fluid chamber through a restricted outlet after said medicament has been delivered; and,
providing delayed feedback to said user once a volume of fluid has passed through the restricted outlet.

These and other aspects will be apparent from and elucidated with reference to the embodiments described hereinafter.

BRIEF DESCRIPTION OF THE FIGURES

Embodiments will now be described, by way of example only, with reference to the accompanying drawings, in which:

FIG. 1A is a schematic side view of an injection device and a removable cap;

FIG. 1B is a schematic side view of the injection device of FIG. 1A, with the cap removed from the housing;

FIG. 2A is a cross-sectional side view of an injection device having a fluid chamber and a membrane, shown before the injection device has been used;

FIG. 2B is a magnified cross-sectional side view of the locking arms of the injection device of FIG. 2A;

FIG. 4C is a cross-sectional side view of the injection device of FIG. 4A and FIG. 4B, shown after the injection device has been used;

FIG. 4D is a magnified cross-sectional side view of the membrane of the injection device of FIGS. 4A, 4B and 4C;

FIG. 5 is a cross-sectional side view of another injection device having a fluid chamber and a whistle;

FIG. 8A is a cross-sectional side view of another injection device having a fluid chamber and a window, shown before the injection device has been used;

FIG. 8B is a cross-sectional side view of the injection device of FIG. 7A, shown after the injection device has been used;

DETAILED DESCRIPTION

Figure 2C:
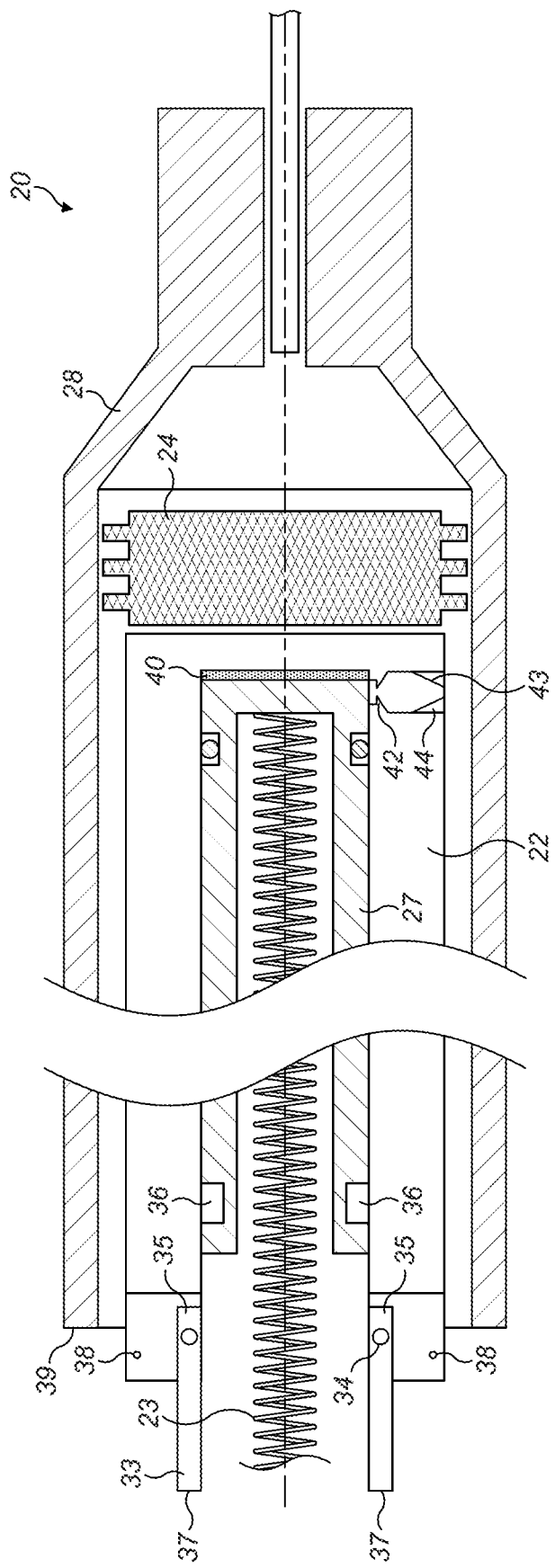
FIG. 2C is a cross-sectional side view of the injection device of FIG. 2A and FIG. 2B, after the injection device has been used.

A drug delivery device, as described herein, may be configured to inject a medicament into a patient. For example, delivery could be sub-cutaneous, intra-muscular, or intravenous. The user of such a device could be a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., up to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 1 cP to about 50 cP. Consequently, a drug delivery device will often include a hollow needle ranging from about 25 to about 31 Gauge in size. Common sizes are 17, 29 and 31 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a syringe 18 containing the medicament to be injected and the components required to facilitate one or more steps of the delivery process. A cap 12 is also provided that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

FIG. 2A, FIG. 2B and FIG. 2C show an example injection device 20 that includes a syringe 28, similar to as described above with reference to FIG. 1A and FIG. 1B. The injection device 20 of FIG. 2A also includes a housing 21, partially shown in FIG. 2A.

As illustrated, the injection device 20 also includes a plunger 22 that acts on the piston 24 to move the piston 24 into the syringe 28 and dispense medicament through the needle (not shown). A drive spring 23 is provided to push the plunger 22 against the piston 24 and into the syringe 28 during use of the injection device 20. The drive spring 23 may be pre-loaded, and a release mechanism may be provided to release the plunger 22 such that the drive spring 23 can push the plunger 22 and piston 24 to dispense medicament, as described previously. It will be appreciated that the piston 24 may be omitted and the end 25 of the plunger 22 may be adapted to act as a piston within the syringe 28.

The injection device 20 of FIG. 2A also includes a delay mechanism that provides delayed user feedback at a time after the plunger 22 has moved into the syringe 28 and medicament has been dispensed. This delayed feedback informs the user that the medicament has been dispensed, and the further delay provides time for the medicament to have dispersed from the injection site.

As illustrated, the injection device 20 of this example includes an actuator, in this example a pusher 27 that is located within the plunger 22. The plunger 22 is elongate and has a cylindrical bore 29 with an opening 30 at the distal end of the plunger 22, in which the pusher 27 is located. The pusher 27 also has a cylindrical bore 31 with an opening 32 at the distal end, and the drive spring 23 is located within the cylindrical bore 31 of the pusher 27. The drive spring 23 acts between a part of the housing 21 and the pusher 27, and urges them apart.

A locking mechanism is provided to hold the plunger 22 and pusher 27 together during initial movement of the plunger 22 into the syringe 28. The locking mechanism has locking arms 33 that fix the pusher 27 relative to the plunger 22, so that the drive spring 23 urges the pusher 27 and plunger 22 into the syringe 28 together.

As illustrated in FIG. 2A and FIG. 2B, each locking arm 33 is pivotally attached to the plunger 22 via pivots 34, and a first end 35 of each locking arm 33 is located in a groove 36 formed in the pusher 27. Arm extensions 37 of the locking arms 33 extend radially of the plunger 22. Stops 38 are arranged on the plunger 22 to prevent rotation of the locking arms 33 as the drive spring 23 urges the pusher 27 and the plunger 22 into the syringe 28. In this way, when the drive spring 23 acts on the pusher 27, the locking arms 33 are trapped between the stops 38 and the grooves 36, and so the pusher 27 and plunger 22 are pushed together into the syringe 28.

As illustrated in FIG. 2C, once the plunger 22 has completed its movement into the syringe 28, i.e. when the medicament has been dispensed, the arm extensions 37 of the locking arms 33 contact the annular end 39 of the syringe 28 and the locking arms 33 are rotated so that the pusher 27 is released from the plunger 22. In particular, the leverage applied to the arm extensions 37 of the locking arms 33 as they are pushed against the annular end 39 of the syringe 28 provides a force adequate to deform or brake the stops 38, allowing the locking arms 33 to rotate and disengage from the grooves 36 in the pusher 27. In alternative examples, the locking arms 33 may abut against another part of the housing 21 instead of the end 39 of the syringe 28.

Therefore, once the plunger 22 has been pushed into the syringe 28 the locking arms 33 rotate and the pusher 27 is free to move independently of the plunger 22 under the force of the drive spring 23.

The locking mechanism may be arranged to release the pusher 27 from the plunger 22 after the plunger 22 has been completely pushed into the syringe 28, i.e. when the piston 24 reaches the end of the syringe 28. Alternatively, the locking mechanism may be arranged to release the pusher 27 from the plunger 22 at a point before the plunger 22 and piston 24 have been completely pushed into the syringe 28, but after an amount of medicament has been dispensed.

As shown in FIG. 2A, prior to using the injection device 20 a fluid chamber 40 is defined between the pusher 27 and the plunger 22, at a distal end of the plunger 22. In particular, the fluid chamber 40 is located in the distal end of cylindrical bore 29 of the plunger 22, and is sealed by the distal end of the pusher 27. The pusher 27 is provided with a sealing ring 41, for example an 'O'-ring, to seal the fluid chamber 40.

Once the locking arms 33 have rotated, as illustrated in FIG. 2C, the pusher 27 is urged further into the cylindrical bore 29 of the plunger, 22 and the fluid chamber 40 is compressed.

The fluid chamber 40 includes an outlet 42 and a passage 44 through the wall of the plunger 22, through which fluid is urged as the pusher 27 compresses the fluid chamber 40. A seal (not shown), for example a thin membrane, may be provided over the outlet 42, and the seal may be broken the pressure of the fluid passing through the outlet 42 as the fluid chamber 40 is compressed. The seal will prevent fluid moving through the outlet 42 until the plunger 22 has completed its movement.

A membrane 43 is located in the passage 44 to the fluid chamber 40 and blocks the fluid passing through the outlet 42 as the pusher 27 compresses the fluid chamber 40. As shown in FIG. 2C, the membrane 43 is inflated by fluid passing through the outlet 42.

In an alternative embodiment, the membrane 43 is located on the opposite side of the passage 44 to the fluid chamber 40, on the outside of the plunger 22.

The inflated membrane 43 may be visible from the exterior of the injection device 20 and thereby provide a visual indication to the user. The membrane 43 may be coloured, or the membrane 43 may be transparent or translucent and the fluid may be coloured. Alternatively, the inflated membrane 43 may burst after receiving an amount of the fluid via the outlet 42, and thereby provide an audible indication to the user. The fluid in the fluid chamber 40, that passes through the outlet 42 and into the membrane, 43 may be a liquid or a gas. For example, the fluid may be water. The fluid may be coloured or transparent.

The outlet 42 comprises a restriction that slows fluid passage through the outlet 42. This restriction ensures that it takes time for the membrane 43 to be inflated and optionally burst, and so the indication is provided to the user at a time after the locking mechanism has released the pusher 27. This delay allows the medicament to disperse from the injection site.

The length of this delay is defined by various factors, such as the size of the outlet 42, the pressure applied to the pusher 27 and fluid chamber 40, the type of fluid used, the viscosity of the fluid used, the bursting strength of the membrane 43, and other such factors. This provides a delayed feedback mechanism, which is started when the pusher 27 is released by the locking arms 33, and completed when the visual and/or audible indication is provided to the user.

The duration of the delay may be, for example, more than 2 seconds, or more than 5 seconds, or more than 10 seconds, or between 10 and 30 seconds, or between 10 and 20 seconds.

In an alternative embodiment similar to that of FIG. 2A to FIG. 2C, the locking arms 33 may be replaced with locking protrusions that protrude from the plunger 22 into the pusher 27, or vice versa, and are configured to be deformed or broken by the force provided by the drive spring 23 once the plunger 22 has been adequately pushed into the syringe 28. In this way, the plunger 22 and pusher 27 move together until the plunger 22 reaches the end of the syringe 28, then the locking protrusions deform or break to permit the pusher 27 to compress the fluid chamber 40 and thereafter provide delayed feedback.

Figure 3:
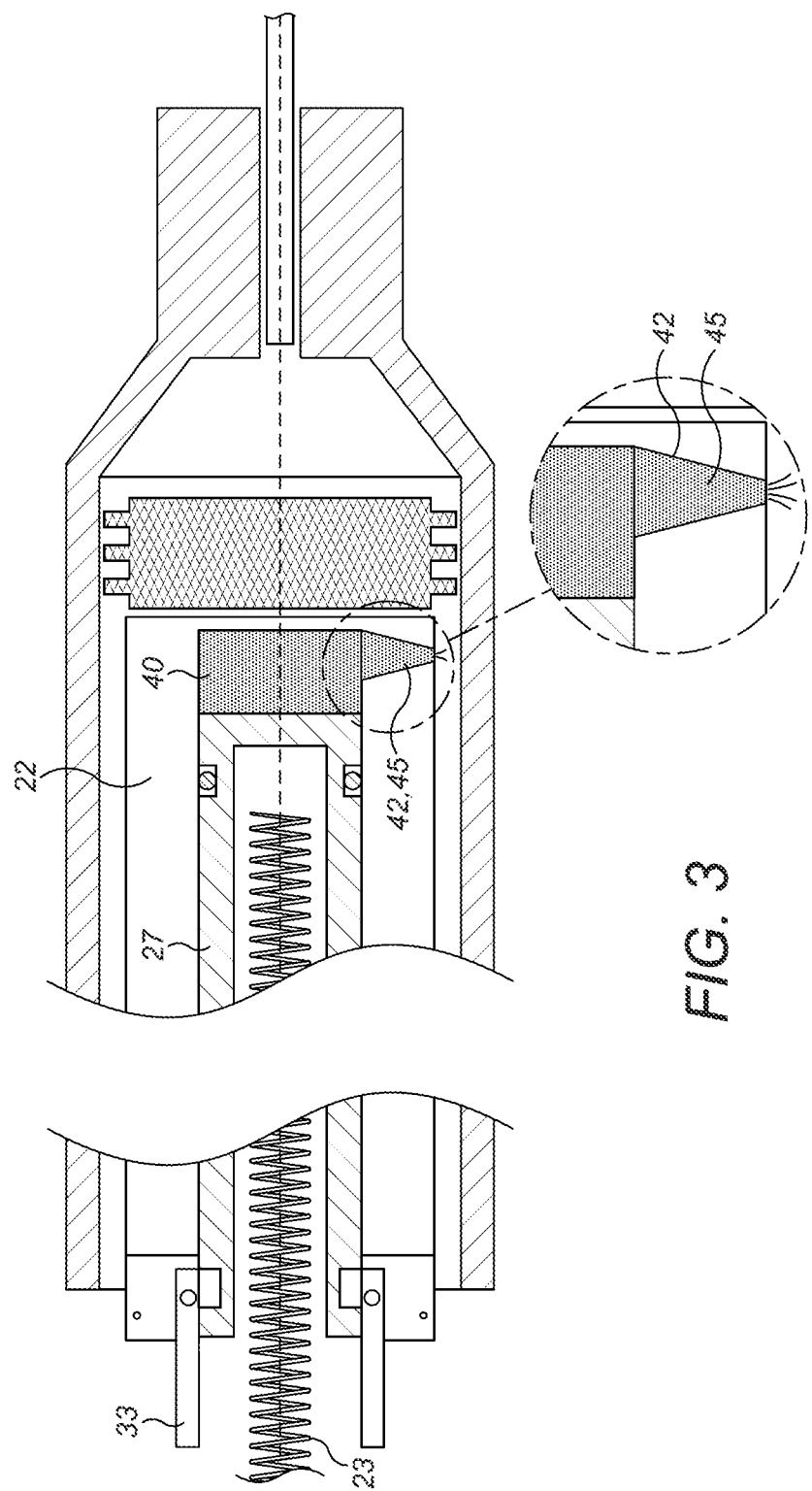
FIG. 3 is a cross-sectional side view of an injection device having a fluid chamber and a whistle.

FIG. 3 shows an alternative example, with the same plunger 22, pusher 27, locking arms 33 and fluid chamber 40 as described with reference to FIG. 2A to 2C. However, in this example the outlet 42 of the fluid chamber 40 and/or the passage 45 through the wall of the plunger 22, is shaped to generated an audible sound, for example a whistling sound. No inflatable membrane is provided.

In this example as the locking arms 33 rotate and release the pusher 27 as previously described, the pusher 27 compresses the fluid chamber 40 and fluid is urged through the outlet 42 and the shaped passage 45 and a whistling sound is generated. The outlet 42 has a restriction to slow fluid flow through the outlet 42 and ensure that the indication is provided at a time after the medicament has been delivered, to allow medicament to disperse from the injection site. In this example, the fluid is preferably a gas.

The feedback mechanism may be configured such that the start of the whistling sound informs the user that the plunger 22 has moved to the end of the syringe 28 and the medicament has been injected, and the end of the whistling sound informs the user that an appropriate amount of time has elapsed to account for dispersion of the medicament from the injection site. The duration of the whistling sound can be determined by various factors, including the size of the fluid chamber 40, the size of the outlet 42, and the force provided by the drive spring 23.

The whistling sound may last for a duration of, for example, more than 2 seconds, or more than 5 seconds, or more than 10 seconds, or between 10 and 30 seconds, or between 10 and 20 seconds.

FIG. 4A to FIG. 4D show an alternative example injection device 46 that includes a syringe 28, similar to as described above with reference to FIG. 1A and FIG. 1B. The injection device 46 of FIG. 4A also includes a housing 21, partially shown in FIG. 4A.

As illustrated, the injection device 46 also includes a plunger 47 that acts on the piston 24 to move the piston 24 into the syringe 28 and dispense medicament from the needle (not shown). A drive spring 23 is provided to push the plunger 47 against the piston 24 and into the syringe 28 during use of the injection device 46. The drive spring 23 may be pre-loaded, and a release mechanism may be provided to release the plunger 47 such that the drive spring 23 can push the plunger 47 and piston 24 to dispense medicament, as described previously. It will be appreciated that the piston 24 may be omitted and the end 25 of the plunger 47 may act as a piston within the syringe 28.

Figure 4A:
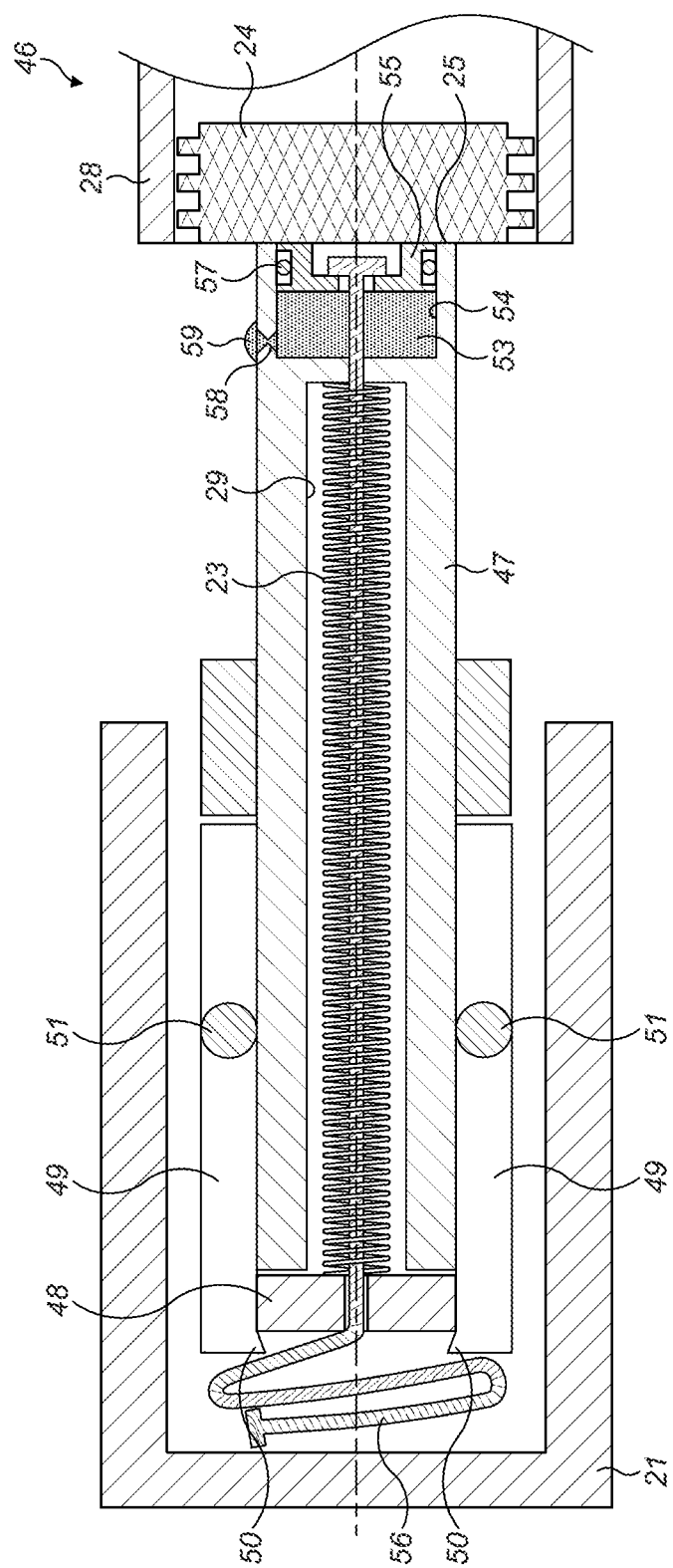
FIG. 4A is a cross-sectional side view of another injection device having a fluid chamber and a membrane, shown before the injection device has been used.

The injection device 46 of FIG. 4A also includes a delay mechanism that provides delayed user feedback at a time after the plunger 47 has moved into the syringe 28 and medicament has been dispensed. This delayed feedback informs the user that the medicament has been dispensed, and the further delay provides time for the medicament to have dispersed from the injection site.

In this example, the plunger 47 has a cylindrical bore 29 that is open at the proximal end, and the drive spring 23 is located in the cylindrical bore 29. An actuator, in this example a carrier 48, is provided near the proximal end of the injection device 46 and the drive spring 23 acts between the plunger 47 and the carrier 48 to urge the plunger 47 distally into the syringe 28 to dispense medicament.

The carrier 48 is initially held in position by a locking mechanism. In particular, locking arms 49 hold the carrier 48 in position. The locking arms 49 have inward deflections 50 at their proximal ends that prevent the carrier 48 moving in a proximal direction. The locking arms 49 are pivotally mounted to the housing 21 about pivots 51, but in the position of FIG. 4A the locking arms 49 are prevented from rotation about the pivots 51 by the presence of the plunger 47. Therefore, in the position shown in FIG. 4A, the drive spring 23 can push on the carrier 48, which is held in place by the locking arms 49.

Figure 4B:
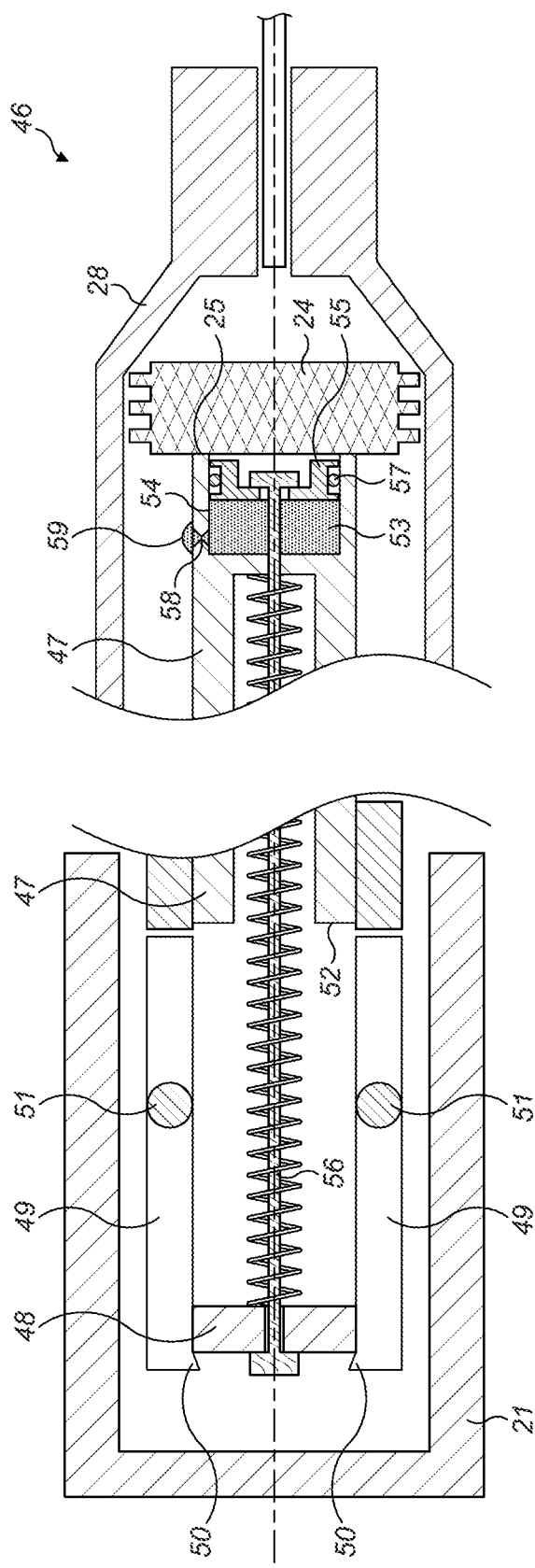
FIG. 4B is a cross-sectional side view of the injection device of FIG. 4A, shown during use.

FIG. 4A illustrates the injection device 46 prior to use, and FIG. 4B illustrates the injection device 46 during use. As shown in FIG. 4B, the drive spring 23 has moved the plunger 47 distally into the syringe 28 and medicament has been dispensed. In this position, with the medicament having been dispensed from the syringe 28, the proximal end 52 of the plunger 47 has moved past the locking arms 49 which are now free to rotate and release the carrier 48, as illustrated in FIG. 4C. The drive spring 23 pushes the carrier 48 against the inward deflections 50, which urges the locking arms 49 to rotate apart to release the carrier 48. The carrier 48 then moves in a proximal direction under the force of the drive spring 23.

The locking mechanism may be arranged to release the carrier 48 after the plunger 47 has been completely pushed into the syringe 28, i.e. when the piston 24 reaches the end of the syringe 28. Alternatively, the locking mechanism may be arranged to release the carrier 48 at a point before the plunger 47 and piston 24 have been completely pushed into the syringe 28, but after an amount of medicament has been dispensed.

A fluid chamber 53 is formed at the distal end 25 of the plunger 47. As illustrated in FIG. 4A, the distal end 25 of the plunger 47 includes a recess 54 in which the fluid chamber 53 is located. A pusher 55 is also located in the recess 54 and is connected to the carrier 48 via a tether 56 that extends through the plunger 47. The pusher 55 seals against the recess 54 to define the fluid chamber 53. As shown, the pusher 55 includes a sealing ring 57, for example an 'O'-ring.

As illustrated in FIG. 4B and FIG. 4C, as the locking arms 49 rotate to release the carrier 48, the carrier 48 is moved proximally by the drive spring 23 and pulls the tether 56, which in turns pulls the pusher 55 proximally and compresses the fluid chamber 53.

The fluid chamber 53 includes an outlet 58 through the wall of the recess 54 of the plunger 47, through which the fluid is urged as the pusher 55 compresses the fluid chamber 53. A seal (not shown), for example a thin membrane, may be provided over the outlet 58, and the seal may be broken by the pressure of the fluid passing through the outlet 58 as the fluid chamber 53 is compressed. The seal will prevent fluid moving through the outlet 58 until the plunger 47 has completed its movement.

A membrane 59 is located at the outlet 58 and blocks the fluid passing out of the fluid chamber 53 as the pusher 55 compresses the fluid chamber 53. As shown in FIG. 4C, the membrane 59 is inflated by fluid passing through the outlet 58.

The inflated membrane 59 may be visible from the exterior of the injection device 46 and thereby provide a visual indication to the user. The membrane 59 may be coloured, or the membrane 59 may be transparent or translucent and the fluid may be coloured. Alternatively, as shown in FIG. 4D, the inflated membrane 59 may burst after receiving an amount of the fluid via the outlet 58, and thereby provide an audible indication to the user. The fluid in the fluid chamber 53, that passes through the outlet 58 and into the membrane 59, may be a liquid or a gas. For example, the fluid may be water. The fluid may be coloured or transparent.

The outlet 58 comprises a restriction that slows fluid passage through the outlet 58. This restriction ensures that it takes time for the membrane 59 to be inflated and optionally burst, and so the indication is provided to the user at a time after the locking mechanism has released the pusher 47. This delay allows the medicament to disperse from the injection site.

The length of this delay is defined by various factors, such as the size of the outlet 58, the pressure applied to the pusher 47 and fluid chamber 53, the type of fluid used, the viscosity of the fluid used, the bursting strength of the membrane 59, and other such factors. This provides a delayed feedback mechanism, which is started when the pusher 47 is released by the locking arms 49, and completed when the visual and/or audible indication is provided to the user.

The duration of the delay may be, for example, more than 2 seconds, or more than 5 seconds, or more than 10 seconds, or between 10 and 30 seconds, or between 10 and 20 seconds.

FIG. 5 shows an alternative example injection device 61, with the same plunger 47, pusher 55 and locking arms 49 as described with reference to FIG. 4A to 4D. However, in this example the outlet 58 of the fluid chamber 53 has a shaped passage 60 that generates an audible sound, for example a whistling sound, as fluid passes through it. No inflatable membrane is provided.

In this example as the locking arms 49 rotate and release the carrier 48, the carrier 48 pulls the pusher 55 via the tether 56 to compress the fluid chamber 53 and fluid is urged through the outlet 58 and the shaped passage 60 and a whistling sound is generated. In this example, the fluid is preferably a gas, for example air or an inert gas.

The delay mechanism may be arranged such that the start of the whistling sound informs the user that the plunger 47 has moved to the end of the syringe 28 and the medicament has been injected, and the end of the whistling sound informs the user that an appropriate amount of time has elapsed to account for dispersion of the medicament from the injection site. The duration of the whistling sound can be determined by various factors, including the size of the fluid chamber 53, the size of the outlet 58, and the force provided by the drive spring 23.

The duration of the whistling sound may be, for example, more than 2 seconds, or more than 5 seconds, or more than 10 seconds, or between 10 and 30 seconds, or between 10 and 20 seconds.

Figure 6B:
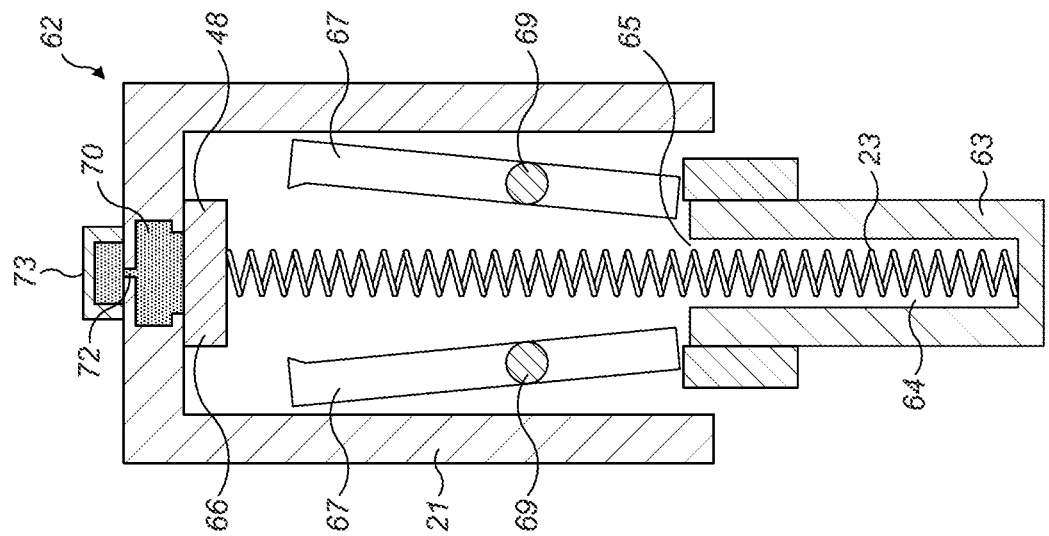
FIG. 6B is a cross-sectional side view of the injection device of FIG. 6A, shown after the injection device has been used.
Figure 6A:
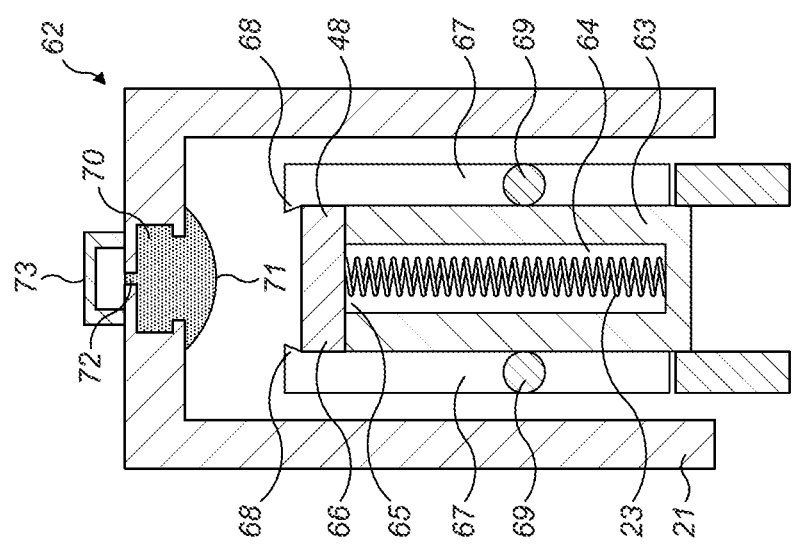
FIG. 6A is a cross-sectional side view of another injection device having a fluid chamber and a window, shown before the injection device has been used.

FIG. 6A and FIG. 6B show an alternative example injection device 62 that includes a syringe (not shown), plunger 63 and actuator (carrier 66), similar to as described above with reference to FIG. 4A to 4C. The injection device 62 of FIG. 6A also includes a housing 21.

As with other examples, the plunger 63 acts on a piston (e.g. 14, see FIG. 1B) to move the piston into the syringe (e.g. 18, see FIG. 1B) and dispense medicament from a needle (e.g. 17, see FIG. 1B). A drive spring 23 is provided to push the plunger 63 against the piston and into the syringe during use of the injection device 62. The drive spring 23 may be pre-loaded, and a release mechanism may be provided to release the plunger 63 and cause the medicament to be dispensed, as described previously.

The injection device 62 of FIG. 6A also includes a delay mechanism that provides delayed user feedback at a time after the plunger 63 has moved into the syringe (e.g. 18, see FIG. 1B). This delayed feedback informs the user that the medicament has been dispensed, and the delay provides time for the medicament to have dispersed from the injection site.

In this example, the plunger 63 has a cylindrical bore 64 that is open at the proximal end 65, and the drive spring 23 is located in the cylindrical bore 64. An actuator, in this example a carrier 66, is provided near the proximal end of the injection device 62 and the drive spring 23 acts between the plunger 63 and the carrier 66 to urge the plunger 63 distally into the syringe (e.g. 18, see FIG. 1B) to dispense medicament.

The carrier 66 is initially held in position by a locking mechanism. In particular, locking arms 67 hold the carrier 66 in position. The locking arms 67 have inward deflections 68 at their proximal ends that prevent the carrier 66 moving in a proximal direction. The locking arms 67 also include pivots 69, but in the position of FIG. 6A the locking arms 67 are prevented from rotation about the pivots 69 by the presence of the plunger 63. Therefore, in the position shown in FIG. 6A, the drive spring 23 can push on the carrier 66, which is held in place by the locking arms 67.

FIG. 6A illustrates the injection device 62 prior to use, and FIG. 6B illustrates the injection device 62 during use. As shown in FIG. 6B, the drive spring 23 has moved the plunger 63 distally and medicament has been dispensed. In this position, with the medicament having been dispensed, the proximal end 65 of the plunger 63 has moved past the locking arms 67 which are now free to rotate and release the carrier 66. In this position, the drive spring 23 pushes the locking arms 67 apart and the inward deflections 68 release the carrier 66. The carrier 66 can therefore move in a proximal direction under the force of the drive spring 23.

The locking mechanism may be arranged to release the carrier 66 after the plunger 63 has been completely pushed into the syringe (e.g. 18, see FIG. 1B). Alternatively, the locking mechanism may be arranged to release the carrier 66 at a point before the plunger 63 has been completely pushed into the syringe (e.g. 18, see FIG. 1B), but after a volume of medicament has been delivered.

As shown, a fluid chamber 70 is located at a proximal end of the housing 21. The fluid chamber 70 is defined by a membrane 71 that holds a fluid on the inside the fluid chamber 70. The proximal end of the housing 21 includes an outlet 72 that is aligned with the fluid chamber 70. A second chamber 73 is located on the outside of the housing 21, aligned with the outlet 72.

Therefore, as illustrated in FIG. 6B, when the carrier 66 is released by the locking arms 67 the carrier 66 is urged proximally and engages and compresses the membrane 71 on the inside of the housing 21. This urges fluid through the outlet 72 and into the second chamber 73.

The second chamber 73 may be transparent, so that the user can see the fluid entering the second chamber 73 as an indication that the plunger 63 has completed its movement into the syringe and an appropriate additional delay has elapsed for medicament to disperse from the injection site. The fluid may be coloured. The fluid may be a liquid, for example water.

The outlet 72 comprises a restriction that slows fluid passage through the outlet 72 and into the second chamber 73. This restriction ensures that it takes time for fluid to reach the second chamber 73, providing a delay between the time the locking mechanism releases the carrier 48 and the time that the indication is provided to the user. This delay allows the medicament to disperse from the injection site.

The length of this delay is defined by various factors, such as the size of the outlet 72, the pressure applied to the pusher 55 and fluid chamber 53, the type of fluid used, the viscosity of the fluid used, and other such factors. This provides a delayed feedback mechanism, which is started when the carrier 48 is released by the locking arms 49, and completed when the visual and/or audible indication is provided to the user.

The duration of the delay may be, for example, more than 2 seconds, or more than 5 seconds, or more than 10 seconds, or between 10 and 30 seconds, or between 10 and 20 seconds.

Figure 7A:
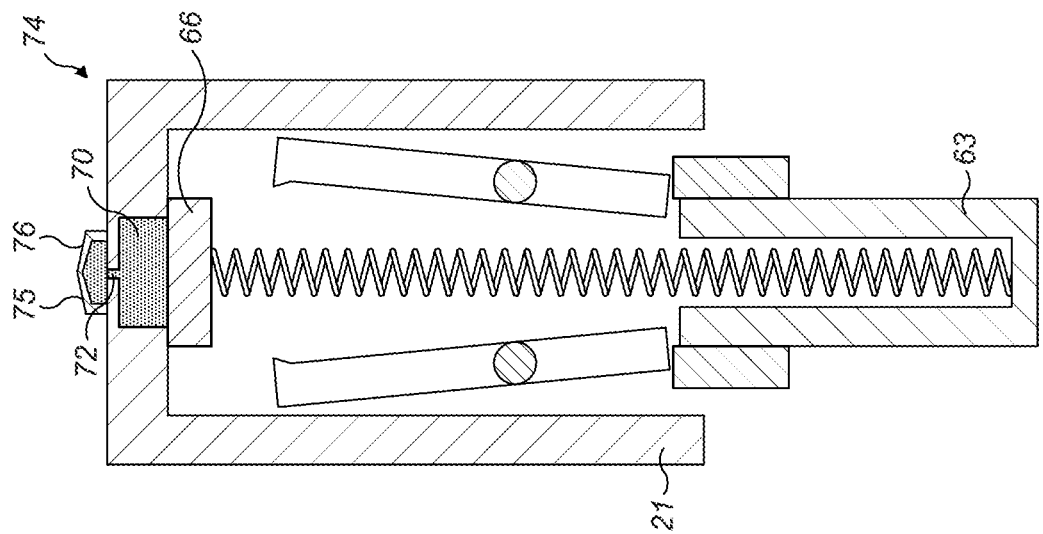
FIG. 7A is a cross-sectional side view of another injection device having a fluid chamber and a window, shown before the injection device has been used.
Figure 7B:
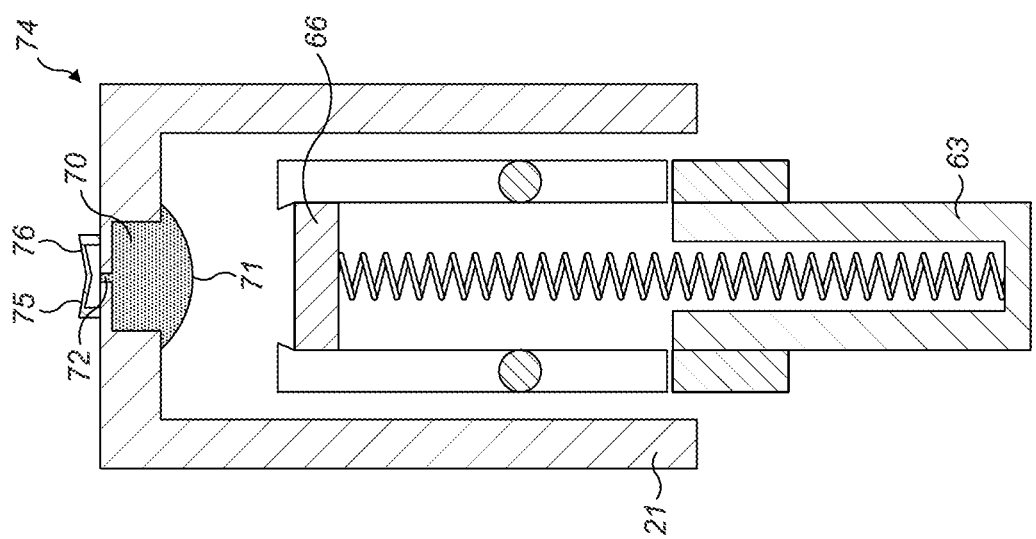
FIG. 7B is a cross-sectional side view of the injection device of FIG. 7A, shown after the injection device has been used.

FIG. 7A and FIG. 7B show a similar example to that of FIG. 6A and FIG. 6B, with a plunger 63, actuator (carrier 66) and a membrane 71 that defines a fluid chamber 70. In this example, the second chamber 75 on the outside of the proximal end of the housing 21 comprises a deflectable wall 76.

In particular, as shown in FIG. 7A, prior to use a deflectable wall 76 of the second chamber 75 is deflected inwards, indicating that the injection device 74 has not been used and/or that it is not ready to be removed from the user. After use, when fluid has been urged through the outlet 72 and into the second chamber 75 by the carrier 66, as illustrated in FIG. 7B, the deflectable wall 76 of the second chamber 75 has been deflected outwards by the increased fluid pressure within the second chamber 75.

The outlet 72 includes a restriction that slows fluid flow through the outlet 72 and therefore delays the time at which the deflectable wall 76 is deflected outwards by the fluid.

This outwardly deflected wall 76 therefore provides an indication that the plunger 63 has completed its movement into the syringe (e.g. 18, see FIG. 1B) and the medicament has been dispensed, and that an appropriate amount of time has elapsed for the medicament to have dispersed from the injection site.

The second chamber 75 may additionally be transparent, so that the user can see the fluid entering the second chamber 75 as an indication that the plunger 63 has completed its movement into the syringe (e.g. 18, see FIG. 1B). The fluid may be coloured. The fluid may be a liquid, for example water.

FIG. 8A and FIG. 8B show a similar example injection device 77 to those of FIG. 6A, FIG. 6B, FIG. 7A and FIG. 7B. The injection device 77 includes a plunger 63, an actuator (carrier 66), and rotatable locking arms 67 that hold the carrier 66 until the plunger 63 has been moved a distance into the syringe (e.g. 18, see FIG. 1B). Once the carrier 66 is released, the drive spring 23 urges the carrier 66 in a proximal direction.

In this example, the proximal end of the housing 21 has a cylindrical protrusion 78 and a piston 79 is provided within the cylindrical protrusion 78 to define a fluid chamber 80. A seal 81 is provided between the piston 79 and the cylindrical protrusion 78. The proximal wall 82 of the housing 21, within the cylindrical protrusion 78, includes an outlet 83. A second chamber 84 is provided on the opposite side of the outlet 83 to the fluid chamber 80. The second chamber 84 is optionally provided with an air outlet 85.

As shown in FIG. 8B, when the carrier 66 is released by the locking arms 67, after the plunger 63 has moved distally, the drive spring 23 urges the carrier 66 against the piston 79, which is pushed into the fluid chamber 80 and urges fluid through the outlet 83 and into the second chamber 84. Air may be displaced from the second chamber 84 through the air outlet 85.

A seal 86 may initially be provided over the outlet 83 to prevent movement of the fluid into the second chamber 84 before the carrier 66 has been released.

The second chamber 84 may additionally be transparent, so that the user can see the fluid entering the second chamber 84 as an indication that the plunger 63 has completed its movement into the syringe (e.g. 18, see FIG. 1B). The fluid may be coloured. The fluid may be a liquid, for example water.

The outlet 83 includes a restriction that slows fluid flow through the outlet 83, thereby delaying the movement of the piston 79, and delaying the indication to the user. This provides a delay for the medicament to disperse from the injection site.

The duration of the delay may be, for example, more than 2 seconds, or more than 5 seconds, or more than 10 seconds, or between 10 and 30 seconds, or between 10 and 20 seconds.

Alternatively or additionally, as illustrated in FIG. 8A and FIG. 8B, the piston 79 may trigger an audible indication to the user. In this example, the piston 79 comprises an arm 87 that protrudes from the piston 79 and engages a sound generator 88. The sound generator 88 is a pre-stressed element that is held in a deflected position by the arm 87 until the piston 79 moves into the fluid chamber 80, at which point the arm 87 disengages the sound generator 88 and the pre-stressed element returns to its natural shape. This changing of shape of the sound generator 88 generates an audible sound, which provides the user with an indication that enough time has elapsed for the medicament to have dispersed from the injection site. In particular the arm 87 does not disengage the sound generator 88 until a volume of fluid has passed into the second chamber 84, which is delayed by the restricted outlet 83, thereby providing a delay in the feedback.

The duration of the delay may be, for example, more than 2 seconds, or more than 5 seconds, or more than 10 seconds, or between 10 and 30 seconds, or between 10 and 20 seconds.

In any of the examples of FIG. 6A to FIG. 8B, a seal may be provided over the outlet 72, 83 that is broken by the pressure provided by the carrier 66 compressing the fluid chamber 70, 80. The seal prevents fluid moving through the outlet 72, 83 prior to use of the injection device 62, 74, 77.

In each of the examples of FIG. 6A to FIG. 8B, the carrier 66 is released at or near the end of the movement of the plunger 63 into the syringe (e.g. 18, see FIG. 1B), when all or nearly all of the medicament has been injected into the user. The arrangement of the fluid chamber 70, 80 and outlet 72, 83 then provides a delay before the user is provided with the indication. This delay allows the medicament to disperse from the injection site before the indication is provided to the user. It is intended that the indication informs the user that they may remove the injection device from the injection site.

Figure 9B:
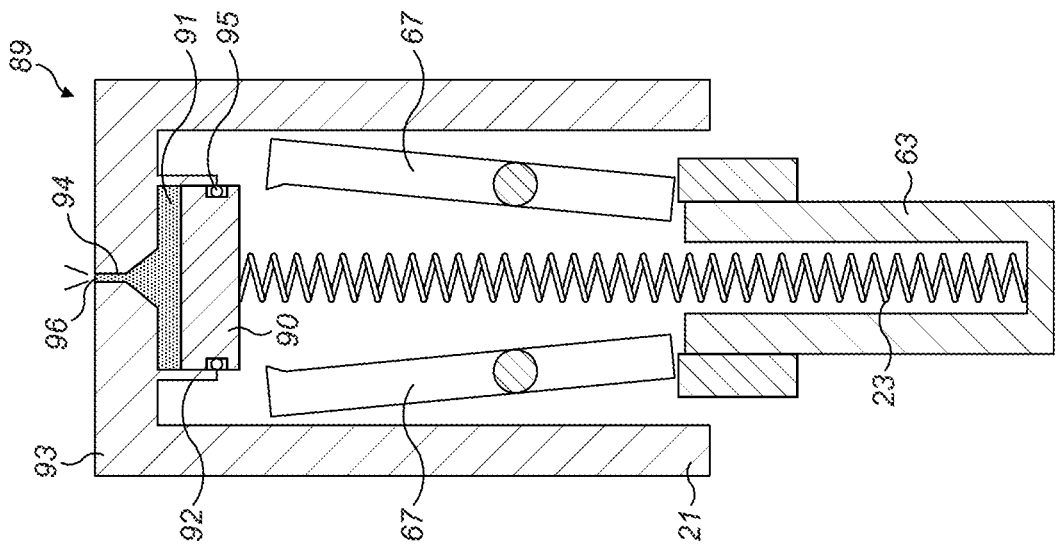
FIG. 9B is a cross-sectional side view of the injection device of FIG. 8A, shown after the injection device has been used.
Figure 9A:
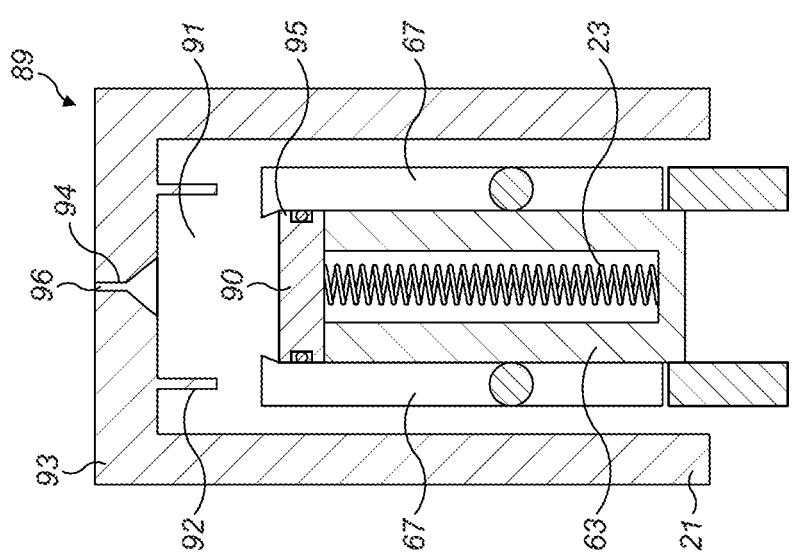
FIG. 9A is a cross-sectional side view of another injection device having a fluid chamber and a whistle, shown before the injection device has been used.

FIG. 9A and FIG. 9B show an alternative example injection device 89, similar to the examples of FIG. 6A to FIG. 8B. In this example the plunger 63, actuator (carrier 90) and locking arms 67 are similar to as described with reference to FIG. 6A to 8B. However, in this example the fluid chamber 91 is not defined by a membrane but by a cylindrical protrusion 92 located on the inside of the proximal end 93 of the housing 21. An outlet 94 passes through the proximal end 93 of the housing 21 to atmosphere—no second chamber is provided as per the examples of FIG. 6A to FIG. 8B.

In this example, once the carrier 90 is released by the locking arms 67 the carrier 90 is pushed into the cylindrical protrusion 92 by the drive spring 23, and the carrier 90 sealably closes a fluid chamber 91, as illustrated in FIG. 9B. The carrier 90 may include a sealing ring 95, for example an 'O'-ring.

The fluid chamber 91 is subsequently compressed by the carrier 90 and fluid, in this example air, is urged through the outlet 94.

The outlet 94 has a shaped passage 96 that generates an audible sound, for example a whistling sound, as fluid passes through it. The outlet 94 also has a restriction that slows fluid flow through the outlet 94, therefore delaying the indication to the user.

The feedback mechanism may be arranged such that the start of the whistling sound informs the user that the medicament has been injected, and the end of the whistling sound informs the user that an appropriate amount of time has elapsed to account for dispersion of the medicament from the injection site. The duration of the whistling sound can be determined by the size of the cylindrical protrusion 92 (and fluid chamber 91), the size of the outlet 94, and the force provided by the drive spring 23.

The duration of the whistling sound may be, for example, more than 2 seconds, or more than 5 seconds, or more than 10 seconds, or between 10 and 30 seconds, or between 10 and 20 seconds.

Figure 10A:
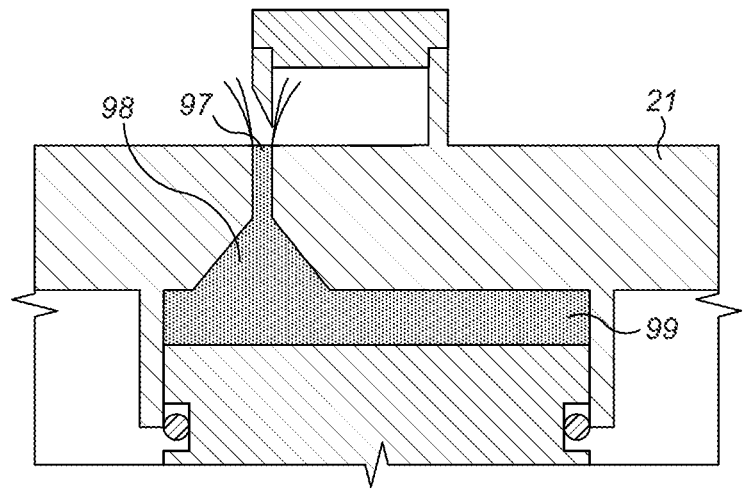
FIG. 10A is a magnified cross-sectional side view of a first whistle for the injection devices of FIG. 3, FIG. 5, and/or FIG. 9A and FIG. 9B; and, FIG. 10B is a magnified cross-sectional side view of a second whistle for the injection devices of FIG. 3, FIG. 5, and/or FIG. 9A and FIG. 9B.
Figure 10B:
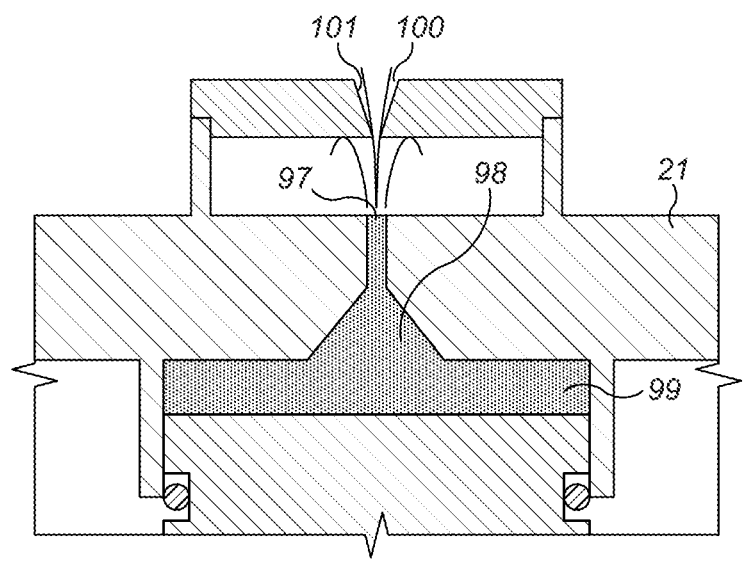

FIG. 10A and FIG. 10B show examples of the configuration of an outlet 97 for generating an audible sound, e.g. whistling. These may be used for the examples of FIG. 3, FIG. 5, or FIG. 9A and FIG. 9B.

In the example of FIG. 10A, the outlet 97 is shaped to generate a hissing or whistling sound as fluid is urged through the outlet 97 from the fluid chamber 99. The outlet 97 has a tapered entry 98 to accelerate fluid flow through the outlet 97 and thereby increase the volume of the sound. In the example of FIG. 10B an amplifier 100 is provided with a funnel shaped passage 101 located in line with the outlet 97 to further amplify the volume of the sound as fluid is urged through the outlet 97.

It will be appreciated that the drive spring of each of the examples described herein may be omitted if the injection device is adapted to be manually operated. For example, the injection device may be provided with a lever or button that the user manually operates to push the plunger into the syringe. In this case, the force provided by the user may be used to subsequently compress the fluid chamber.

In any of the above-described examples, the delay between the beginning of compression of the fluid chamber and the indication being provided to the user may be increased by using a highly viscous, or non-Newtonian fluid. This reduces the rate at which the fluid can pass through the outlet during compression of the fluid chamber and thereby delays the indication to the user.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen-injector, auto-injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, chamber, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A feedback mechanism for an injection device, the injection device configured to deliver a medicament to a user, the feedback mechanism comprising:
    an actuator;
    a fluid chamber having a restricted outlet, wherein the actuator is configured to urge fluid from the fluid chamber through the restricted outlet, and wherein the actuator is moveable relative to the fluid chamber between a first position and a second position, and wherein the restricted outlet comprises a restriction that slows fluid passage through the restricted outlet such that the fluid flows within the restricted outlet at a reduced flow rate; and
    an indicator configured to provide feedback to the user after a predetermined volume of fluid has passed from the fluid chamber through the restricted outlet during use of the injection device;
    wherein the indicator comprises a passage configured to create an audible sound as fluid passes through the passage.

2. The feedback mechanism of claim 1, wherein the indicator comprises a membrane configured to be inflated by fluid passing through the restricted outlet.

3. The feedback mechanism of claim 2, wherein the membrane is configured to burst as a result of fluid passing through the restricted outlet.

4. The feedback mechanism of claim 1, wherein the indicator comprises a second chamber configured to receive fluid passing through the restricted outlet.

5. The feedback mechanism of claim 4, wherein at least a part of the second chamber is configured to be displaced by fluid being received by the second chamber.

6. The feedback mechanism of claim 4, wherein at least a part of the second chamber is transparent or translucent such that the user can see fluid being received by the second chamber.

7. The feedback mechanism of claim 1, wherein the actuator comprises an actuator element.

8. The feedback mechanism of claim 7, further comprising a biasing member configured to urge the actuator element.

9. The feedback mechanism of claim 1, wherein the actuator is moveable relative to the fluid chamber between a first position and a second position.

10. The feedback mechanism of claim 1, wherein the actuator is moveable within the fluid chamber.

11. The feedback mechanism of claim 1, wherein the restricted outlet comprises an orifice configured such that fluid can be urged through the orifice.

12. The feedback mechanism of claim 1, wherein the fluid comprises a gas.

13. The feedback mechanism of claim 1, wherein the fluid comprises a liquid.

14. A method of using an injection device, the method comprising:
    delivering medicament to a user;
    urging fluid from a fluid chamber through a restricted outlet after the medicament has been delivered by moving an actuator from a first position to a second position, wherein the restricted outlet comprises a restriction that slows fluid passage through the restricted outlet such that the fluid flows within the restricted outlet at a reduced flow rate; and providing a delayed feedback to the user once a predetermined volume of fluid has passed through the restricted outlet, wherein the injection device comprises a feedback mechanism, wherein the feedback mechanism comprises an indicator comprising a passage, and wherein providing the delayed feedback to the user comprises creating an audible sound at the indicator in response to fluid passing through the passage.

15. The method of claim 14, wherein the indicator comprises a membrane, and wherein the method further comprises inflating the membrane with the fluid passing through the restricted outlet.

16. The method of claim 15, wherein providing the delayed feedback to the user comprises bursting the membrane with the fluid passing through the restricted outlet.

17. The method of claim 14, wherein the indicator comprises a second chamber, and wherein the method further comprises receiving fluid passing through the restricted outlet in the second chamber.

18. The method of claim 17, further comprising displacing at least a part of the second chamber with the fluid received in the second chamber.

19. The method of claim 14, wherein the fluid comprises a gas.

20. The method of claim 14, wherein the fluid comprises a liquid.

* * * * *